United States Patent [19] — Lenz et al.

[11] Patent Number: 4,753,913
[45] Date of Patent: Jun. 28, 1988

[54] GAS-PHASE ALKYLATION OF PHENOLS, AND A CATALYST FOR THIS PURPOSE

[75] Inventors: Hans-Heinrich Lenz, Mannheim; Eckhard Roske, Ludwigshafen; Karl Baer, Weinheim, all of Fed. Rep. of Germany

[73] Assignee: BASF Aktiengesellschaft, Fed. Rep. of Germany

[21] Appl. No.: 883,180

[22] Filed: Jul. 8, 1986

[30] Foreign Application Priority Data

Jul. 8, 1985 [DE] Fed. Rep. of Germany ....... 3524331

[51] Int. Cl.⁴ .............................................. B01J 21/10
[52] U.S. Cl. .................................... 502/183; 502/184; 568/804
[58] Field of Search ................. 568/804, 798; 502/183, 502/184

[56] References Cited

U.S. PATENT DOCUMENTS

| | | | |
|---|---|---|---|
| 3,446,856 | 5/1969 | Hamilton | 568/804 |
| 3,446,865 | 5/1969 | Roth et al. | 568/804 |
| 3,953,529 | 4/1976 | Yonemitsu et al. | 568/804 |
| 3,968,172 | 7/1976 | Ichikawa et al. | 568/804 |
| 4,165,439 | 8/1979 | Smith | 568/804 |
| 4,227,023 | 10/1980 | Kawamata et al. | 568/804 |
| 4,283,574 | 8/1981 | Leach | 568/804 |
| 4,359,591 | 11/1982 | Fremery et al. | 568/804 |
| 4,418,224 | 11/1983 | Bennett et al. | 568/804 |
| 4,482,758 | 11/1984 | Seig | 568/804 |
| 4,503,272 | 4/1985 | Bennett et al. | 568/804 |
| 4,528,507 | 7/1985 | Smith et al. | 568/804 |
| 4,551,563 | 11/1985 | Talley | 568/804 |
| 4,590,307 | 3/1986 | Bennett et al. | 568/804 |

FOREIGN PATENT DOCUMENTS

| | | | |
|---|---|---|---|
| 465655 | 6/1950 | Canada | 502/183 |
| 38371 | 10/1981 | European Pat. Off. | 568/804 |
| 0019476 | 1/1984 | European Pat. Off. | 568/804 |
| 150311 | 11/1984 | European Pat. Off. | 568/804 |
| 129065 | 12/1984 | European Pat. Off. | 568/804 |
| 1263010 | 3/1968 | Fed. Rep. of Germany | 568/804 |
| 2415930 | 10/1974 | Fed. Rep. of Germany | 568/804 |
| 2428056 | 2/1977 | Fed. Rep. of Germany | 568/804 |
| 2716035 | 11/1977 | Fed. Rep. of Germany | 568/804 |
| 2853452 | 3/1983 | Fed. Rep. of Germany | 568/804 |
| 3012357 | 3/1983 | Fed. Rep. of Germany | 39/7 |
| 3149022 | 6/1983 | Fed. Rep. of Germany | 568/804 |
| 3228713 | 2/1984 | Fed. Rep. of Germany | 568/804 |
| 902043 | 7/1962 | United Kingdom | 502/183 |
| 1034500 | 6/1966 | United Kingdom | 568/804 |
| 2033776 | 5/1980 | United Kingdom | 502/183 |
| 2089343 | 6/1982 | United Kingdom | 568/804 |

*Primary Examiner*—Werren B. Lone
*Attorney, Agent, or Firm*—Keil & Weinkauf

[57] ABSTRACT

The proposed catalyst for the gas-phase alkylation of phenols is based on magnesium oxide, contains up to 0.4% by weight of alkali metal oxide and is mechanically stabilized with from 1 to 8% by weight, based on the total weight of the catalyst, of graphite, molded and then heated.

7 Claims, No Drawings

GAS-PHASE ALKYLATION OF PHENOLS, AND A CATALYST FOR THIS PURPOSE

The present invention relates to a process for the gas-phase alkylation of phenols, and a catalyst for this purpose. The gas-phase alkylation is carried out by reacting a phenol, which carries hydrogen in one and/or two ortho positions, with an alcohol in the presence of the stated catalyst, the corresponding phenol alkyl-substituted in the ortho position being obtained.

The literature describes a large number of systems which catalyze this alkylation. However, the known catalyst systems all possess disadvantages with regard to one or more of the following characteristics:
Activity
Ortho selectivity (ie. yield for alkylation in the ortho position, based on converted phenol)
Alkanol selectivity
Life
Maximum thickness of the catalyst tube
Mechanical stability
Necessity of additives in the catalyst or feed (inert material).

For example, U.S. Pat. No. 3,446,856 describes a catalyst which is based on magnesium oxide and has a life of only from 75 to 100 hours and a methanol selectivity of only from 40 to 50%. The alumina-based catalyst described in U.S. Pat. No. 2,448,942 has the disadvantage of a low ortho selectivity. British patent No. 1,034,500 describes a magnesium oxide catalyst which requires reaction temperatures of above 500° C. and is therefore not very active. The magnesium oxide catalyst described in DE-B-1 263 010 has the disadvantage that it cannot be brought into a mechanically stable form. A catalyst based on Fe/Si/Cr, as described in DE-A-2 428 056, is toxicologically unacceptable. The catalyst system according to DE-A-3 228 713, which consists of Fe/Si/Mg, can be used in an oven which has to be capable of being heated in a plurality of zones in order to be able to carry out the reaction isothermally. DE-A-3 149 022 describes a catalyst system which is based on Fe/Cr/Ce and requires special measures to keep the temperature differences small (less than 5° C.) in order to avoid decomposition of methanol. These measures comprise narrow tube cross-sections (<50 mm), dilution of the catalyst and dilution of the educt, in each case with inert material. The catalyst system of DE-C-3 012 357 is a complicated four-component system consisting of Fe/Si/Cr/alkaline earth metal. Its disadvantage is the fact that methanol has to be used in a large excess over phenol. Moreover, decomposition of the methanol takes place. DE-A-2 853 452 describes a catalyst system which consists of Mn/Si/alkaline earth metal and to which a suitable inert gas, such as nitrogen or carbon dioxide, has to be added in order to allow the reaction to take place smoothly. This in turn makes working up more difficult. EP-B-19 476 describes a catalyst system which consists of iron and gallium and has the disadvantage that the methanol selectivity is less than 70%. The catalyst system based on Mg/Ti/sulfate and described in U.S. Pat. No. 4,283,574 possesses low ortho selectivity. DE-A-2 716 035 relates to a catalyst, based on copper and chromium, which has the disadvantage that it possesses low activity at low temperatures (250°–300° C.). If the temperature is raised (for example to 325° C.) in order to increase the conversion, virtually complete methanol decomposition occurs.

The catalyst described in GB-B-2 089 343 and based on Fe/Cu and chromium has the disadvantage that its activity and selectivity are lost after only a short operating time.

It is an object of the present invention to provide a magnesium oxide-based catalyst for the gas-phase alkylation of phenols which does not have the stated disadvantages and in particular has a long life coupled with high yield and selectivity, without loss of activity. It is a further object of the present invention to provide a process for the gas-phase alkylation of phenols, using a catalyst of this type.

We have found that this object is achieved by a catalyst of the type described at the outset, which has an alkali metal content, expressed as alkali metal oxide, of up to 0.4% by weight and is mechanically stabilized with from 1 to 8% by weight, based on the total weight of the catalyst, of graphite, molded and heated.

Phenols used in the process for gas-phase alkylation are those which carry hydrogen in one or both positions ortho to the hydroxyl group and are reacted with alcohols using a catalyst based on magnesium oxide. In the process, the catalyst has an alkali metal oxide content of up to 0.4% by weight and is mechanically stabilized with from 1 to 8% by weight, based on the total weight of the catalyst, of graphite, molded and heated.

In a preferred embodiment of the catalyst, the alkali metal oxide content is from 0.05 to 0.2, in particular 0.1, % by weight, based on the total weight of the catalyst. Sodium ions constitute a preferred alkali metal component, but it is also possible to use other alkali metal ions, for example those of lithium, potassium, rubidium and cesium.

The catalyst is mechanically stabilized with from 1 to 8% by weight of graphite, and molded. A graphite content of from 1.5 to 3, in particular about 2, % by weight, based on the total weight of the catalyst, is preferred.

The catalyst may have any conventional shape and may be in the form of, for example, rings, pellets, spheres or cones.

The novel catalyst is preferably molded by pelletizing. Heating is then carried out at from 550° to 700° C., preferably from 600° to 650° C., for an adequate period, preferably 1 hour.

Surprisingly, the novel catalyst does not possess the disadvantages described at the outset in connection with the prior art. The conversions are virtually quantitative, high ortho selectivity being ensured. The catalyst has a remarkably long life. Even after an operating time of 2000 hours, there is scarcely any marked reduction in activity, and the selectivity is retained.

Changes in composition lead to a deterioration in the catalyst properties. Lower alkali metal contents result in a shorter life, while higher alkali metal contents cause a reduction in activity and methanol selectivity.

Graphite contents lower than those stated make pelletizing more difficult. Higher graphite contents reduce the life, the activity and the ortho selectivity. Other organic pelletizing assistants likewise reduce the life and activity. Inorganic pelletizing assistants are unsuitable.

Extrudates are mechanically unstable. Heating at low temperatures results in lower ortho selectivity, while heating at temperatures higher than those mentioned leads to deactivation.

In the novel process for gas-phase alkylation, the starting mixture consisting of phenol, an alkanol and, if required, water is vaporized in a conventional manner and fed to the reactor. The catalyst is advantageously arranged in a tube. The temperature is brought to 400°–500° C., preferably 420°–480° C., by means of a heating medium, for example a salt bath.

In the novel process for gas-phase alkylation, sharp temperature increases, ie. hot spots, are avoided without any dilution effect or additional heating zones. For example, in the reaction of phenol and methanol, the methanol selectivity of 85–95% is consequently higher than the methanol selectivities in the conventional processes. Since no hot spots occur, catalyst tubes having a diameter of >50 mm can be used.

In the process according to the invention, the phenol conversion is virtually quantitative. The ortho selectivity is >95% and, after an operating time of a few days, is as high as 97–98%.

If, after a very long operating time, the activity of the novel catalyst decreases, regeneration may be effected in the reaction tube, using a nitrogen/oxygen mixture.

In the novel process for gas-phase alkylation, it is possible to use phenols which carry hydrogen in one or both positions ortho to the hydroxyl group. Unsubstituted phenol or substituted phenols, unsubstituted naphthol, eg. α-naphthol, or substituted naphthols may be used, unsubstituted phenol being particularly preferred.

The alcohols used may be primary, secondary or tertiary aliphatic, saturated or unsaturated alcohols, examples being methanol, ethanol, n-propanol, isopropanol, n-butanol, isobutanol, tert.-butanol, sec.-butanol, pentanols, hexanols, octanols and decanols. Methanol, ethanol and isopropanol are particularly preferred.

The novel process can be used to convert the following phenols to the corresponding useful products, for example using methanol:

phenol to o-cresol and/or 2,6-dimethylphenol, o-cresol to 2,6-dimethylphenol, m-cresol or 2,3-dimethylphenol to 2,3,6-trimethylphenol, p-cresol to 2,4,6-trimethylphenol, 3,5-dimethylphenol to 2,3,5,6-tetramethylphenol, 3,4-dimethylphenol to 2,4,5-trimethylphenol, 2,3,4-trimethylphenol to 2,3,4,6-tetramethylphenol, 2,5-dimethylphenol to 2,3,6-tri-methylphenol, and 4-tert.-butylphenol to 2,6-dimethyl-4-tert.-butylphenol.

The reaction of α-naphthol with methanol may give, for example, 2-methyl-α-naphthol.

If phenol is reacted with ethanol, it is possible to prepare, for example, 2-ethylphenol and 2,6-diethylphenol.

If phenol is reacted with isopropanol, 2-isopropylphenol, for example, can be prepared.

If it is intended to prepare the dialkyl derivative from a phenol, the monoalkyl derivative initially formed can be recycled to the reactor.

The catalyst according to the invention has an alkali metal content of from 0 to 0.4% by weight, calculated as alkali metal oxide and based on the total weight of the catalyst.

The Example which follows and Comparative Examples 1 to 3 illustrate the invention.

EXAMPLE

A heatable fixed-bed reactor is filled with 450 ml of a magnesium oxide which contains 0.1% of $Na_2O$ and has been pelletized with 2% of graphite to give 5 mm particles and heated for 1 hour at 650° C. 442.5 g/h of a mixture of phenol, o-cresol, methanol and water in a molar ratio of 1:1:10:4, in the form of a vapor, are passed over a 60 cm long catalyst zone at a catalyst temperature of 465° C., under atmospheric pressure. The reaction mixture which emerges is condensed, and the gaseous part, which mainly consists of hydrogen, carbon monoxide, carbon dioxide and methane, is removed. After the methanol and the water have been removed by distillation, a residue of the following composition remains:

1.6% of phenol
31.1% of o-cresol
66.9% of 2,6-dimethylphenol.

The ortho selectivity and methanol selectivity are 98% and 89%, respectively. The catalyst does not show the slightest loss of activity after an operating time of 42 days.

COMPARATIVE EXAMPLE 1

50 ml of a magnesium oxide which contains 0.1% of $Na_2O$ and has been pelletized with 2% of graphite to give 2–3 mm particles and heated for 1 hour at 750° C. are introduced into a fixed-bed reactor. 59.4 g/h of a mixture of phenol, o-cresol, methanol and water in a molar ratio of 1:1:10:4, in the form of a vapor, are passed over the 60 cm long catalyst zone. Owing to the fairly low catalyst activity, the temperature in the catalyst zone has to be brought to 520° C. When the discharged mixture is condensed and then worked up, the following are obtained:

13.8% of phenol
68.8% of o-cresol
15.5% of 2,6-dimethylphenol.

The ortho selectivity and methanol selectivity are 96% and 41%, respectively. Even at the beginning of the 15-day operating period, the catalyst shows a gradual loss of activity.

COMPARATIVE EXAMPLE 2

A magnesium oxide which is doped with 1.0% of $Na_2O$ and has been pelletized with 2% of graphite and heated at 650° C. for 1 hour is used. The reaction conditions correspond to those of Comparative Example 1. Working up the condensate gives 26.9% of phenol
59.6% of o-cresol
7.7% of 2,6-dimethylphenol.

The ortho selectivity and methanol selectivity are 90.3% and 37%, respectively. The catalyst is incapable of maintaining the initially low activity level over an operating time of 5 days.

COMPARATIVE EXAMPLE 3

A magnesium oxide which contains 0.1% of $Na_2O$ and has been pelletized with 10% of graphite and heated at 650° C. for 1 hour is tested as described in Comparative Example 1, but at 490° C. When the discharged mixture is condensed and worked up, the following are found:

5.2% of phenol
55.8% of o-cresol
36.5% of 2,6-dimethylphenol.

The ortho selectivity and methanol selectivity are 96% and 42.2%, respectively. The catalyst shows a substantial decrease in activity in the course of an operating time of 30 days.

We claim:

1. A molded catalyst for the gas-phase alkylation of phenols, said catalyst consisting essentially of magnesium oxide, form 0.05 to 0.4% of an alkali metal, expressed as alkali metal oxide, and from 1 to 8% by weight of graphite.

2. A catalyst as defined in claim 1, wherein the alkali metal oxide content is from 0.05 to 0.2% by weight.

3. A catalyst as defined in claim 1, which contains sodium ions as the alkali metal component.

4. A catalyst as defined in claim 1, which contains from 1.5 to 3% by weight of graphite.

5. A catalyst as defined in claim 1, which is obtainable by heating at from 550° to 700° C.

6. A catalyst as defined in claim 1, which is molded by pelletizing.

7. The catalyst of claim 1, wherein the catalyst is heated after molding at a temperature of from 550° to 700° C.

* * * * *